United States Patent [19]

Ryde et al.

[11] 3,968,201

[45] July 6, 1976

[54] DOSAGE UNIT CONTAINING A SUBSTANCE SHOWING A TOPICAL EFFECT ON THE EYE, AND A METHOD OF PREPARING SAME

[75] Inventors: Emma Märta Ryde; Jan Erik Ekstedt, both of Uppsala, Sweden

[73] Assignee: Pharmacia Aktiebolag, Uppsala, Sweden

[22] Filed: Nov. 18, 1974

[21] Appl. No.: 525,031

Related U.S. Application Data

[62] Division of Ser. No. 416,717, Nov. 16, 1973, Pat. No. 3,868,445.

[30] Foreign Application Priority Data

Nov. 30, 1972  Sweden............................ 15652/72

[52] U.S. Cl................................... 424/14; 424/19; 424/22; 424/78; 424/83; 128/260; 128/261; 128/271; A61K/9/52; A61K/31/745
[51] Int. Cl.²...................... A61K 9/02; A61K 9/06
[58] Field of Search.................... 424/78–83, 424/14, 16, 19–22; 128/260, 261, 271

[56] References Cited
UNITED STATES PATENTS

| | | | |
|---|---|---|---|
| 2,627,938 | 2/1953 | Frohmader et al. | 183/45 |
| 2,628,187 | 2/1953 | Frohmader et al. | 424/83 X |
| 2,628,205 | 2/1953 | Shoemaker | 260/29.6 |
| 2,775,561 | 12/1956 | Frohmader | 252/308 |
| 3,215,599 | 11/1965 | Thau et al. | 424/83 |
| 3,574,827 | 4/1971 | Beerbower | 424/83 |
| 3,670,065 | 6/1972 | Eriksson et al. | 264/131 |
| 3,868,445 | 2/1975 | Ryde et al. | 424/14 |

FOREIGN PATENTS OR APPLICATIONS 1,070,593  6/1967  United Kingdom

OTHER PUBLICATIONS

Horsch et al. Chem. Abst. 52 No. 15830h (1958) "Washable Ointment Bases Formulated With Polyethylene".
Elsner et al. Chem. Abst. 75 No. 25343a (1971) "Use of Polyethylene Gel in Ophthalmic Ointment Containing Pilocarpine Hydrochloride".
Tice Chem. Abst. 22 No. 4723$^{(7)}$ (1928) "Notes on Three Ointments".
Wild Chem. Abst. 8 No. 989$^{(3)}$ (1914) "The official Ointments... Soft Paraffin as an Ointment Basis".
Thau et al. J. Soc. Cosmetic Chemists 16: 359–363 (1965) "A New Procedure for the Preparation of Polyethylene–Mineral Oil Gels".
Mutimer et al. J. A. Ph. A. Sci. Ed. XLV: 101–105, 212–218 (1956) "Modern Ointment Base Technology III".
Martin et al. J. A. Ph. A. Prac. Phy. Ed. XIV: 230–231 (1953) "Petrocera–A Versatile Ointment Base".
Lesser Drug & Cosm. Ind. 63 (3): 318–320, 402–407 (1948) "Ophthalmic Ointments".

*Primary Examiner*—Shep K. Rose
*Attorney, Agent, or Firm*—Fred Philpitt

[57] ABSTRACT

A composition in the form of a solid shaped body adapted for insertion in the cavity of the eye and containing a substance having a topical effect on the eye, which composition comprises a mixture of 5 – 90 % of at least one lipophilic substance having a melting point of 37° – 75°C, 0 – 40 % of at least one water-soluble or water-swellable polymer in solid, finely-divided form, 0.05 – 30 % of at least one drug having a topical effect on the eye and 0.2 – 20 % of at least one water-insoluble lipophilic polymer having a softening temperature exceeding 70°C and a melting point exceeding 85°C and which is soluble in the lipophilic substance or substances in molten form to serve as stabilizer for the mixture, the percentages relating to percent by weight calculated on the total weight of the mixture.

19 Claims, No Drawings

DOSAGE UNIT CONTAINING A SUBSTANCE SHOWING A TOPICAL EFFECT ON THE EYE, AND A METHOD OF PREPARING SAME

This application is a division of our prior application Ser. No. 416,717 filed Nov. 16, 1973, (now U.S. Pat. No. 3,868,445) and the benefits afforded by 35 USC 120 and 121 are claimed relative to said prior application.

The present invention relates to a dosage unit for drugs showing a topical effect on the eye and to a method for the preparation of said dosage unit.

In eye treatment in connection with eye diseases the drugs have up to now usually been administered in the form of eye drops or ointments. These forms of administration are afflicted with great disadvantages i.a. due to the fact that the dosage becomes ununiform. Ointments are only useful in practice for use at night since they settle in the form of a thin coat on the eye. The well known adhesive properties of the ointments are also a disadvantage and they are difficult to keep sterile during a consumption period.

It is also known to apply tetracaine to eyes in the form of lamellae of gelatin when the eyes have become subjected to welding flashes. The gelatin lamella has the disadvantage to be hard and brittle and to form sharp edges. Gelatin also gives pain when applied to the eye.

The preparation of hydrophilic contact lenses is also known by means of which lenses the application of drugs has been suggested to be possible (Mladá Fronta, Vol. 23: 310 (7088), Nov. 10, 1967). It has appeared that too fast a release of the drug from such preparations is obtained. Trouble in the form of microbial infection is also known in connection with hydrophilic contact lenses.

An object of the present invention is to remove the disadvantages incident to the use of the above preparations.

The present invention relates to a method in the preparation of a dosage unit for a drug showing a topical effect on the eye and comprising a solid, shaped-body intended to be inserted in the cavity of the eye. The method is mainly characterized in that the solid, shaped body is formed from a mixture of 5 – 90 % of at least one lipophilic substance having a melting point of 37° – 75°C, such as a higher hydrocarbon, a wax or a fat or a mixture thereof having a melting point within the aforementioned range, 0 – 40 % of at least one water-soluble or water-swellable polymer in solid, finely divided form, such as lower alkyl-cellulose, polyvinyl alcohol, polyvinyl pyrrolidone, dextrin, dextran or starch, 0.05 – 30 % of at least one medicament showing a topical effect on the eye, and 0.2 – 20 % of at least one water-insoluble lipophilic polymer which has a softening temperature exceeding 70°C, preferably lying within the range of 80° – 200°C, and having a melting point exceeding 85°C, preferably exceeding 100°C, and which is soluble in the lipophilic substance or substances in molten form, the lipophilic polymer preferably being an aliphatic polymer, such as polyvinyl acetate, ethylene-vinylacetate-copolymer, polybutylmethacrylate, aliphatic hydrocarbon polymer, for example polyethylene, polypropylene or ethylenepropylene-copolymer or mixtures thereof to serve as a stabilizer for the mixture, the percentages being percentages by weight calculated on the total weight of the mixture and the constituents of the mixture being dispersed with each other and a solid, shaped body being prepared from said mixture by moulding, pressing or punching techniques, said shaped body having a largest dimension between the limits 2 and 20 mm, preferably between the limits 6 and 16 mm.

The present invention enables substances showing a topical effect on the eye to be administered in a highly convenient way. Thus, it is possible, for example, to administer substances for glaucoma therapy in an advantageous manner without any irritation, whereby a uniform effect of long duration is obtained as opposed to substances previously used, such as eye drops, ointments and solid preparations. The expression "eye cavity" as used here and in the claims refers to the space between the eye and the surrounding tissue, e.g. the space beneath each eyelid.

The lipophilic substance or substances having a melting point of 37° – 75°C may comprise, for example, a higher hydrocarbon, a wax or a fat or mixtures of such substances. There is preferably selected a lipophilic substance or mixtures of such substances having a melting point of 38° – 55°C, which in combination with the polymer or polymers soluble therein softens slightly at body temperature without melting. In this way any irritation caused by the shaped-body when placed in the eye cavity is extremely slight. Preferably 20 – 90 % of the lipophilic substance or substances is used.

When the lipophilic substances used have the form of hydrocarbons, mixtures can be used which, for example, comprise mainly n-paraffins and, to a lesser extent, isomers thereto, said mixtures being obtained for example by distilling petroleum. The wax used may, for example, be bees wax, which is a mixture of mainly triacontanolpalmitate, n-hexacosanoic acid ($C_{26}H_{52}O_2$) and hydrocarbons. By fats is primarily meant glycerol esters of fatty acids having 8 – 22 carbon atoms, preferably 10 – 18 carbon atoms. For example, so-called hard fat (Pharm. Nord.) may be used.

The water-soluble or water-swellable polymer or polymers may contain, for example, hydroxyl groups and/or amino groups and/or amide groups and/or carboxyl groups. There are preferably used water-soluble polymers which dissolve subsequent to preceding swelling. Mixtures of two or more such polymers may also be used. Examples of such polymers include dextran, lower hydroxy-alkyl dextran, carboxy-methyl dextran, lower hydroxy-alkyl cellulose, lower alkyl-cellulose, carboxy-methyl cellulose, polyvinyl alcohol, dextrin, starch; polyvinyl pyrrolidone and polyalkylene glycols. The particle size of the solid polymer is preferably selected within the range of approximately 150 $\mu$ and approximately 5 $\mu$, for example approximately 150 $\mu$ to approximately 30 $\mu$ (e.g. smaller than 100 mesh and greater than 550 mesh).

The water-insoluble lipophilic polymers having a softening temperature exceeding 70°C, preferably a softening temperature within the range 80 – 200°C, and having a melting point exceeding 85°C, preferably exceeding 100°C, which is soluble in the lipophilic substance or substances in molten form, preferably have the form of an aliphatic polymer. Examples of such aliphatic polymers include primarily aliphatic hydrocarbon polymers, such as polyethylene, polypropylene, or ethylene-propylene-copolymers. Other examples include polyvinylacetate, ethylene-vinylacetate-copolymers, polybutylmethacrylate. Mixtures of two or more such polymers may also be used.

The substance showing a topical effect on the eye is preferably a drug for glaucoma therapy. Examples of such drugs for use in the present context include primarily pilocarpine. Other examples are adrenaline, physostigmine and synstigmine, and ascorbic acid and guanetidine. Examples of other substances showing a topical effect on the eye and suitable for inclusion in the composition of the present invention are substances having a mydriatic effect such as metaoxedrin, atropin and chemotherapeutics, such as sulfonamides, e.g. sulfisoxazole and sulfametizole, and antibiotics, such as chloramphenicol and tetracycline and glycocorticoids, such as hydrocortisone and prednisolone, and antivirus agents, such as idoxuridine and antihistamines. In suitable cases, the substances may be used in the form of physiologically acceptable salts. Mixtures of said substances may also be used. If the drug showing topical effect on the eye is in a solid, finely-divided form, the selected particle size preferably lies within the range of approximately 150 $\mu$ to approximately 5 $\mu$, for example approximately 150 $\mu$ to approximately 30 $\mu$ (e.g. smaller than 100 mesh and greater than 550 mesh).

Naturally, all constituents of the dosage unit are selected from substances which are physiologically acceptable in the eye cavity when using the dosage unit.

In accordance with the invention, the solid shaped body has a largest dimension between the limits 2 – 20 mm, preferably between the limits 6 – 16 mm. The remaining dimensions of the unit preferably lie within the limits 0.4 – 16 mm, such as within the limits 0.5 – 10 mm, the smallest dimension preferably lying between the limits 0.5 and 5 mm, for example within the limits 0.8 – 3 mm. The weight of the body preferably lies within the limits 0.02 – 0.25 g, e.g. within the limits 0.05 – 0.19 g.

The dosage unit for substances having a topical effect on the eye in accordance with the invention, is mainly characterized in that the unit comprises a solid, shaped body intended to be inserted in the cavity of the eye, said body being formed from a mixture of 5 – 90 % of at least one lipophilic substance having a melting point of 37° – 75°C, such as a higher hydrocarbon, a wax or a fat or a mixture of such substances, having a melting point within the aforementioned range, 0 – 40 % of at least one water-soluble or water-swellable polymer in solid, finely-divided form, such as lower alkylcellulose, polyvinyl alcohol, polyvinyl pyrrolidone, dextrin, dextran or starch, 0.05 – 30 % of at least one drug showing topical effect on the eye and 0.2 – 20 % of at least one water-insoluble lipophilic polymer having a softening temperature exceeding 70°C, preferably a softening temperature lying within the limits 80°– 200°C and having a melting point exceeding 85°C, preferably exceeding 100° C which is soluble in the lipophilic substance or substances in molten form, the lipophilic polymer preferably being an aliphatic polymer such as polyvinyl acetate, ethylene-vinylacetate-copolymer, polybutyl methacrylate, aliphatic hydrocarbon polymer, such as polyethylene, polypropylene or ethylene-propylene-copolymer or mixtures thereof acting to stabilize the mixture, the percentages being percentages by weight calculated on the total weight of the mixture, wherewith the ingredients of the mixture are dispersed with each other and wherein a solid, shaped body is prepared from the mixture by moulding, pressing or punching techniques, said body having a largest dimension between the limits of 2 and 20 mm, preferably between the limits of 6 and 16 mm.

In order to obtain a mixture from which the solid bodies are formed, the ingredients may be dispersed together in finely divided solid form. This mixture can then be formed into the desired bodies by pressing, moulding or punching techniques using suitable shaping tools. One convenient method of producing the mixture from which the bodies are formed is to disperse the hydrophilic polymer or polymers in solid finely divided form and the drug or drugs showing topical effect on the eye preferably also in solid, finely divided form, in a melt of the lipophilic substance or substances and the water insoluble lipophilic polymer or polymers. The melt is then molded (with the solid substances homogeneously dispersed therein) in separate doses in suitable moulds, which may simultaneously serve as a packeting means and which may be sealed in a sterile environment, or is moulded to a thin flat plate, from which separate doses can be punched and transferred in a suitable package in a sterile environment. Subsequent to being punched out of the flat sheet, the edges of the bodies may be rounded in different ways, e.g. by carefully heating and melting the material at the cut surface. The package may be designed so that when used only the dosage unit to be used at any one time is released, while the remaining dosage units remain in their sterile environment. Because the solid body contains no water, there is little risk of microbial growth therein.

If desired the mixture can be admixed with other substances, such as physiologically acceptable salts and/or antimicrobial substances, e.g. preserving agents, which may have a solid, finely divided form or may be dissolved in the lipophilic substance melt.

When forming the solid bodies, they are given softly rounded corners so as not to cause irritation to the eye when inserted into the eye cavity and subsequent to such insertion. The solid bodies may be given different shapes. When the mixture is plastic, then planar, parallel elongated bodies having rounded ends or ellipsoidal plates can be made, preferably by being punched from a flat, thin sheet, the thus obtained bodies as a result of their plasticity forming themselves to the shape of the eye cavity when inserted into the eye. If the plasticity of the mixture is not so pronounced as with the aforementioned case, the solid body may suitably be given a convex or a concave surface, suitably by moulding the body in a suitable mould, so that the body obtains the shape of a lens capable of fitting into the space between the eye and the surrounding tissues, the concave surface of the body being faced towards the eye. Alternatively, the body may be given two convex surfaces.

One simple manner of obtaining a unit presenting a convex and a concave surface and having rounded edges is to use the aforementioned moulding technique, the bottom of the mould being shaped so as to give the body a convex surface, while the concave surface is obtained by adjusting the surface tension of the melt, the melt thereby obtaining an adjusted contact angle to the wall of the mould and with subsequent solidification of the melt a concave surface is obtained on the upper free surface of the melt.

The aforedescribed bodies or units constitute a highly advantageous dosage unit for drugs showing local effect on the eye, since the drug is released slowly and continuously from said units. The rates of release of the drug can be varied by varying the quantities of the ingredients of the unit. For example, the speed at which the drug is released may be selected so that only one or two doses need be administered each day. The interval between doses may be made longer by selecting a slower release. Because of the slow release of the drug, it is possible to avoid the overdoses of short duration obtained with the previously mentioned eye drops. In order to obtain a somewhat reduced effect immediately after inserting the unit beneath the eyelid, the outer surface of the unit may be partly depleted of the drug in question. This can be achieved by subjecting the unit to a short treatment period, with a liquid, e.g. an aqueous liquid, in which the drug is soluble, so that a portion of the drug is leached from the outermost layer of the unit. Another method is to coat the surface of the units with a thin layer through which the drug can penetrate and which contains no drugs or which contains a lower concentration of the drug than the main body of the unit. The layer, for example, may have a similar composition as the main body of the unit but with a lower drug content or may contain no drugs at all.

It is possible to control still further the speed at which the substance showing topical effect on the eye is released from a unit according to the invention, by coating one side of the unit with an impermeable film or a film which is slowly dissolved without forming solid residues.

If the unit contains a water-soluble or water-swellable polymer in solid, finely divided form the polymer upon contact with fluid in the eye cavity will dissolve into a viscous solution or gel-like envelope around the unit. The shape of the unit, its plastics properties and the lubricating envelope co-act to prevent mechanical irritation of the eye by the unit and ensure that instead of remaining in a specific position said unit will occasionally change its position within the eye cavity, which is to advantage. Furthermore, the gel envelope forms a diffusion barrier for the drug for glaucoma therapy and therewith prevents a local overdose with subsequent irritation.

To facilitate insertion of the unit into the eye cavity an applicator in the form of a cylindrical rod may be used, the rod having an accurately chamfered portion at one end thereof in which a diametrically extending slot is located. This slot is used as means for retaining the unit when administering the dose. The applicator is conveniently made of a soft, elastic material. After use, and before inserting the next unit, the administered unit is readily removed, by carefully pulling the eye lid away from the eye, whereafter the patient leans forward and the unit falls out.

The units containing the drug in accordance with the invention have been found to possess a very advantageous combination of properties. The shaped bodies release in the eye cavity the drug in a very favourable way so that a uniform and protracted therapeutical effect is obtained. The shaped body also has extremely advantageous plastic properties by means of which it does not irritate or damage the sensitive eye cavity because of the combination of the lipophilic polymer and the lipophilic substance having a melting point of 37°– 75°C. The favourable properties have been proven in vitro as well as in vivo with, for example, drugs for glaucoma therapy showing a topical effect on the eye, such as pilocarpine hydrochloride for example. The use of shaped bodies according to the invention thus involves a great improvement in comparison with compositions used hitherto.

The invention will now be described and illustrated with reference to a number of examples.

EXAMPLE 1

A mixture was prepared from the following ingredients:

| | |
|---|---|
| Paraffin, solid (melting points 46 – 48°C) | 85.0 % |
| Polyethylene (softening temperature approx. 110°C, does not melt at this temperature) | 2.5 % |
| Pilocarpine hydrochloride (particle size <100 mesh) | 12.5 % |
| | 100.0 % |

The solid paraffin was melted at approximately 90°C and the polyethylene was immersed into the hot melt whilst stirring with a turbine agitator or magnet agitator. The clear melt was then cooled to approx. 60°C, whereafter powderous pilocarpine hydrochloride was added in small portions whilst stirring the mix, agitation being adapted so that no air bubbles occurred in the melt. Subsequent to adding all the powder, the melt was stirred more roughly for a further 30 minutes, so that a homogeneous suspension melt was obtained. The melt was spread onto a heated flat surface into a uniform layer having a thickness of approx. 1.5 mm. The thickness of the layer was corrected by placing a sheet of metal or silicon or the like at a distance of 1.4 mm from the other flat surface, or — in an alternative case — by passing a scraper over the layer at a determined distance from said underlying plate. The suspension melt was then cooled to 20°C, whereupon a thin slab was obtained from which ellipsoidal or rod-shaped flat units having rounded corners were punched out by means of a punch provided with heated cutting zones or — in an alternative case — by means of an unheated punch, wherewith the resulting cut surface was then treated with radiation heat or melted by passing the divided dose through a layer of heated silicon oil, for example. In this case there was used to advantage a tool which gives the unit a largest dimension of approximately 12 mm and a next largest dimension of approximately 5 mm. The smallest dimension, which was then adjusted by the distance between the aforementioned plates, was approx. 1.4 mm. The weight of the units in this instance was approx. 0.06 g. Alternatively, the dimensions of the unit may be approximately 15 mm, 3.5 mm and 1.4 mm, the weight of the unit in this case being slightly less than the weight of the aforementioned unit. The whole manufacturing process was carried out aseptically. The units thus obtained were divided out into sterilized packets, which were heat sealed.

EXAMPLE 2

A mixture was prepared from the following ingredients:

| | |
|---|---|
| Paraffin, solid (melting point 46 – 48°C) | 68 % |
| Polyethylene (softening temperature approx. 100°C, does not melt at this temperature) | 2 % |
| Dextran, average molecular weight approx. 8000 (particle size <100 mesh) | 20 % |
| Pilocarpine hydrochloride (particle size <100 mesh) | 10 % |
| | 100 % |

A suspension melt was prepared in accordance with Example 1. The melt was then transferred to a double-wall container having drainage means and an agitator. The double-wall container was heated by circulating hot water (58° – 60°C) in the space between the two walls without coming into contact with the melt. Determined doses of the melt were tapped off from the container. The tapped doses were caught in specially designed moulds and caused to solidify therein by cooling the moulds. The moulds were designed to provide a convex surface on the unit by adjusting the melt to the shape of the mould. The unit was also given a concave surface, which was formed by the surface tension of the melt and the contact angle to the mould, or by pressing an overlying mould against the semi-solidified mixture, to thereby produce a concave surface on the unit. The moulds may also be designed to produce units having flat, parallel surfaces. Moulds thus designed may also serve as a packaging means for the finished unit. The whole of the manufacturing procedure is effected aseptically in sterile rooms with sterilized apparatus and sterile substances, or alternatively the packaged end product may be radiation sterilized. The mould used is, to advantage, one which imparts to the unit a largest dimension of approx. 13 mm and a smallest dimension of approx. 2.5 mm, the remaining dimension being approx. 7.5 mm. The weight of the unit obtained with Example 2 is approx. 0.12 g.

Upon insertion of a unit in the eye cavity of a test subject, practically constant effect on the accommodation on the eye was obtained during the whole test period. The test was carried out over a period of 18 hours.

EXAMPLE 3

A mixture was prepared from the following ingredients:

| | |
|---|---|
| Paraffin, solid (melting point 46 – 48°C) | 67.5 % |
| Polyethylene (softening temperature approx. 110°C, does not melt with this temperature) | 20.0 % |
| Pilocarpine hydrochloride (particle size <100 mesh) | 12.5 % |
| | 100.0 % |

The units were prepared and produced in a manner analogous with that described with reference to Example 2.

EXAMPLE 4

A mixture was prepared with the following ingredients:

| | |
|---|---|
| Paraffin, solid (melting point 46 – 48°C) | 77.7 % |
| Polybutylmethacrylate (softening temperature approx. 90°C, does not melt at this temperature) | 2.3 % |
| Pilocarpine hydrochloride (particle size <100 mesh) | 20.0 % |
| | 100.0 % |

The units were prepared and produced from the mixture in a manner analogous with that described with reference to Example 1 and Example 2.

EXAMPLE 5

A mixture was prepared from the following ingredients:

| | |
|---|---|
| Paraffin, solid (melting point 46 –48°C) | 72.8 % |
| Polypropylene (softening temperature approx. 170°C, does not melt at this temperature) | 2.2 % |
| Pilocarpine hydrochloride (particle size <100 mesh) | 25.0 % |
| | 100.0 % |

The units were prepared and produced from the mixture in a manner analogous with that described with reference to Example 1 and Example 2.

EXAMPLE 6

A mixture was prepared from the following ingredients:

| | |
|---|---|
| Paraffin, solid (melting point 46 – 48°C) | 85.0 % |
| Ethylene-vinylacetate-copolymer (softening temperature approx. 100°C, does not melt at this temperature) | 2.5 % |
| Pilocarpine hydrochloride (particle size <100 mesh) | 12.5 % |
| | 100.0 % |

The units were prepared and produced from the mixture in a manner analogous with that described with reference to Example 1 or Example 2.

EXAMPLE 7

This test was carried out analogously with the test shown in Example 6, although propylene-ethylene copolymer was used instead of the ethylene-vinylacetate-copolymer. The polymer used had a softening temperature of approx. 150°C, which is below the melting point of said polymer.

EXAMPLE 8

A mixture was prepared from the following ingredients:

| | |
|---|---|
| Paraffin, solid (melting point 46 – 48°C) | 68 % |
| Polyethylene (softening temperature approx. 110°C, does not melt at this temperature) | 2 % |
| Polyvinyl alcohol (Gelvatol 20–60, particle size <100 mesh) | 20 % |
| Pilocarpine hydrochloride (particle size <100 mesh) | 10 % |
| | 100 % |

The units were prepared and produced from the mixture in a manner analogous to that described with reference to Example 1 or Example 2.

EXAMPLE 9

A mixture was prepared from the following ingredients:

| | |
|---|---|
| Paraffin, solid (melting point 46 – 48°C) | 68 % |
| Polyethylene (softening temperature approx. 110°C, does not melt at this temperature) | 2 % |
| Methylcellulose (1500 cp) (particle size <100 mesh) | 20 % |
| Pilocarpine hydrochloride (particle size <100 mesh) | 10 % |
| | 100 % |

The units were prepared and produced from the mixture in a manner analogous to that disclosed with reference to Example 1 or Example 2.

EXAMPLE 10

This example was carried out analogously with Example 2, although dextrin was used instead of dextran.

The units were formed in a manner analogous with that disclosed with reference to Examples 1 or 2.

EXAMPLE 11

This example was carried out analogously with Example 2, although starch was used instead of dextran.

EXAMPLE 12

This example was carried out analogously with Example 1, although sulfametizole (particle size <100 mesh) was used instead of pilocarpine hydrochloride.

EXAMPLE 13

This example was carried out analogously with Example 1, although adrenaline bitartrate (particle size <100 mesh) was used instead of pilocarpine hydrochloride.

EXAMPLE 14

This example was carried out analogously with Example 1, although hydrocortisone acetate (particle size <100 mesh) was used instead of pilocarpine hydrochloride.

EXAMPLE 15

This example was carried out analogously with Example 1, although chloramphenicol (particle size <100 mesh) was used instead of pilocarpine hydrochloride.

EXAMPLE 16

This example was carried out analogously with Example 1, although idoxuridine (particle size <100 mesh) was used instead of pilocarpine hydrochloride.

EXAMPLE 17

A mixture was prepared from the following ingredients:

| Ingredient | % |
|---|---|
| Wax (Pharm. Nord.) | 78.5 % |
| Polyethylene (softening temperature 110°C, does not melt at this temperature) | 1.5 % |
| Dextran (average molecular weight $M_w$ 8000, particle size <100 mesh) | 10.0 % |
| Pilocarpine hydrochloride (particle size <100 mesh) | 10.0 % |
| | 100.0 % |

The units were prepared and produced from the mixture in a manner analogous with that disclosed with reference to Example 2.

EXAMPLE 18

A mixture was prepared from the following ingredients:

| Ingredient | % |
|---|---|
| Paraffin, solid (melting point 46 – 48°C) | 70 % |
| Polyethylene (softening temperature approx. 110°C, does not melt at this temperature) | 5 % |
| Pilocarpine hydrochloride (particle size <100 mesh) | 25 % |
| | 100 % |

The units were prepared and produced from the mixture in a manner analogous to that described with reference to Examples 1 or 2.

The units obtained in accordance with the invention have been tested in vitro and in vivo.

With the in vitro test, release of the drug from the units was tested when the units were immersed in water and in 0.9 % solution of sodium chloride in water.

With one in vitro test, 1.5 % of the drug was released during the first hour from a unit prepared in accordance with Example 2, and a total of 15 % during 24 hours. From a unit prepared in accordance with Example 18, 1.5 % of the drug was released during the first two hours and a total of 5.2 % was released during 24 hours.

With in vivo tests, the pupil reducing effect of pilocarpine and its ability to affect accommodation of a normal eye were used as test parameters. With one such test using a unit prepared in accordance with Example 2, a good effect on both the pupil and the accommodation of the eye was obtained practically constantly during the 18 hours over which the in vivo test was continued. With another test using a unit prepared according to Example 18, a good effect on both the pupil and accommodation was obtained during the 24 hours over which the test was continued.

What we claim is:

1. An opthalmic composition in the form of a solid shaped body having a largest dimension between the limits of 2 – 20 mm and remaining dimensions within the range of 0.5 – 10 mm, with softly rounded corners so as not to cause eye irritation, the body being either planar or suitably molded to obtain the shape of a lens capable of fitting into the space between the eye and the surrounding tissue with a surface facing toward the eye, said solid shaped body as a result of its plasticity forming itself to the shape of the eye cavity when inserted into the eye, said body comprising a mixture of:
   a. 5 – 90% of at least one lipophilic substance having a melting point of 46° – 75°C and being selected from the group consisting of higher hydrocarbons, waxes, fats and mixtures thereof, having a melting point within the aforementioned range,
   b. 0 – 40% of at least one water-soluble or water-swellable polymer in solid, finely-divided form,
   c. 0.05 – 30% of at least one drug showing a topical effect on the eye,
   d. 0.2 – 20% of at least one water-insoluble lipophilic polymer having a softening temperature exceeding 70°C and a melting point exceeding 85°C and which is soluble in the lipophilic substance or substances in molten form to serve as stabilizer for the mixture, the percentages relating to percent by weight calculated on the total weight of the mixture.

2. A composition according to claim 1 wherein the lipophilic substance has a melting point of at least 46°C.

3. A composition according to claim 1 wherein the lipophilic substance is a solid paraffin having a melting point of 46° – 48°C.

4. A composition according to claim 1 which contains 20 – 90% of the lipophilic substance.

5. A composition according to claim 1 which contains 67.5 – 90% of the lipophilic substance.

6. A composition according to claim 2 which contains 20 – 90% of the lipophilic substance.

7. A composition according to claim 2 which contains 67.5 – 90% of the lipophilic substance.

8. A composition according to claim 3 which contains 20 – 90% of the lipophilic substance.

9. A composition according to claim 2 which contains 67.5 – 90% of the lipophilic substance.

10. A composition according to claim 1 wherein the lipophilic substance or substances comprises paraffin, hard fat, or beeswax.

11. A composition according to claim 1 wherein the drug showing a topical effect on the eye is selected from the group consisting of pilocarpine, atropine, metaoxedrin, adrenaline, physositgmine, synstigmine, guanetidine, ascorbic acid, chloramphenicol, sulfamethizole, hydrocortisone and, in suitable cases, salts thereof, and mixtures thereof.

12. A composition according to claim 1 wherein at least one surface of the solid, shaped body is convex.

13. A composition according to claim 1 wherein the drug showing topical effect on the eye is in solid, finely-divided form.

14. A composition according to claim 1 wherein the solid shaped body has a largest dimension lying between the limits 6 and 16 mm.

15. A composition according to claim 1, wherein the lipophilic polymer is selected from the group consisting of polyvinyl acetate, ethylene-vinylacetate-copolymer, polybutyl methacrylate, polyethylene, polypropylene, ethylene-propylene-copolymer and mixtures thereof.

16. A composition according to claim 1 which contains 1.5 – 20% of at least one water insoluble lipophilic polymer.

17. A composition according to claim 1 wherein said water-soluble or water swellable polymer is present in an amount of about 20%.

18. A composition according to claim 1 wherein said water-soluble or water-swellable polymer is dextran present in amount of about 20%.

19. A composition according to claim 1 wherein said water-soluble or water-swellable polymer is polyvinyl alcohol and is present in an amount of about 20%.

* * * * *